US012623090B2

(12) United States Patent (10) Patent No.: US 12,623,090 B2
Bilston et al. (45) Date of Patent: May 12, 2026

(54) SYSTEMS, DEVICES AND METHODS FOR THE TREATMENT OF ORAL AND PHARYNGEAL DISORDERS

(71) Applicants: Lynne Bilston, Ashfield (AU); Peter Burke, Redfern (AU)

(72) Inventors: Lynne Bilston, Ashfield (AU); Peter Burke, Redfern (AU)

(*) Notice: Subject to any disclaimer, the term of this patent is extended or adjusted under 35 U.S.C. 154(b) by 59 days.

(21) Appl. No.: 17/059,649

(22) PCT Filed: May 29, 2019

(86) PCT No.: PCT/AU2019/050532
§ 371 (c)(1),
(2) Date: Nov. 30, 2020

(87) PCT Pub. No.: WO2019/227150
PCT Pub. Date: Dec. 5, 2019

(65) Prior Publication Data
US 2021/0260398 A1     Aug. 26, 2021

(30) Foreign Application Priority Data
May 31, 2018     (AU) ................................. 2018901953

(51) Int. Cl.
*A61N 5/06*          (2006.01)
*A61N 1/04*          (2006.01)
*A61N 5/067*         (2006.01)

(52) U.S. Cl.
CPC ......... *A61N 5/0603* (2013.01); *A61N 1/0452* (2013.01); *A61N 1/0456* (2013.01);
(Continued)

(58) Field of Classification Search
CPC .. A61N 5/0603; A61N 1/0452; A61N 1/0456; A61N 5/062; A61N 5/0622;
(Continued)

(56) References Cited

U.S. PATENT DOCUMENTS 5,792,067 A * 8/1998 Karell ................ A61N 1/36031
607/42
8,562,658 B2 10/2013 Shoham et al.
(Continued)

FOREIGN PATENT DOCUMENTS

JP        2014528265 A    10/2014
WO       2008124918 A1    10/2008
(Continued)

OTHER PUBLICATIONS

Fleury Curado T, Fishbein K, Pho H, Brennick M, Dergacheva O, Sennes LU, Pham LV, Ladenheim EE, Spencer R, Mendelowitz D, Schwartz AR, Polotsky VY. Chemogenetic stimulation of the hypoglossal neurons improves upper airway patency. Sci Rep. Mar. 10, 2017;7:44392. doi: 10.1038/srep44392. (Year: 2017).*
(Continued)

*Primary Examiner* — William J Levicky
(74) *Attorney, Agent, or Firm* — John A. Zurawski; The Belles Group, P.C.

(57)          ABSTRACT

Herein are provided systems, devices, and methods for the treatment of oral and pharyngeal disorders via the stimulation of pharyngeal muscles. Contraction of the pharyngeal muscle cells (9) is induced by activation of at least one ion channel (1) formed in at least one of a muscle cell and a neural cell. The ion channel opens (4) when it is activated by a stimulus (3). This allows ions to flow into (5) and out of (6) the cell, causing muscle contraction. This muscle contraction can be targeted towards specific muscles depending upon the condition to be treated.

28 Claims, 7 Drawing Sheets

(52) U.S. Cl.
CPC ........... *A61N 5/062* (2013.01); *A61N 5/0622* (2013.01); *A61N 2005/0606* (2013.01); *A61N 2005/0626* (2013.01); *A61N 2005/063* (2013.01); *A61N 5/067* (2021.08)

(58) Field of Classification Search
CPC ............ A61N 5/067; A61N 2005/0606; A61N 2005/0626; A61N 2005/063; A61N 2005/0663; A61N 2/004; A61N 5/0601; A61N 2/002; A61N 2/006; A61N 2005/0645; C12N 2750/14143; A61F 5/566; A61B 5/08; A61B 5/24; A01K 67/0275; A01K 2227/105; A01K 2267/03; A61C 7/08; A61M 2202/206

See application file for complete search history.

(56) References Cited

U.S. PATENT DOCUMENTS

| | | | |
|---|---|---|---|
| 8,718,776 B2 * | 5/2014 | Mashiach ............ | A61N 1/0514 |
| | | | 607/42 |
| 9,101,759 B2 | 8/2015 | Delp et al. | |
| 9,308,392 B2 | 4/2016 | Deisseroth et al. | |
| 10,213,600 B2 | 2/2019 | Tyler | |
| 10,470,921 B2 | 11/2019 | Radmand | |
| 10,583,309 B2 | 3/2020 | Deisseroth et al. | |
| 10,729,524 B2 | 8/2020 | Brawn et al. | |
| 11,191,663 B2 | 12/2021 | Radmand | |
| 2007/0239055 A1 * | 10/2007 | Sowelam ................. | A61B 5/08 |
| | | | 600/529 |
| 2007/0250119 A1 * | 10/2007 | Tyler ................. | A61N 1/36103 |
| | | | 607/2 |
| 2010/0262212 A1 | 10/2010 | Shoham et al. | |
| 2011/0060266 A1 * | 3/2011 | Streeter ............... | A61N 5/0613 |
| | | | 604/20 |
| 2011/0166632 A1 | 7/2011 | Delp et al. | |
| 2013/0072999 A1 | 3/2013 | Mashiach et al. | |
| 2013/0085537 A1 | 4/2013 | Mashiach | |
| 2013/0289675 A1 | 10/2013 | Deisseroth et al. | |
| 2014/0039579 A1 | 2/2014 | Mashiach et al. | |
| 2014/0046408 A1 | 2/2014 | Shoham et al. | |
| 2014/0324133 A1 | 10/2014 | Deisseroth et al. | |
| 2015/0140502 A1 * | 5/2015 | Brawn ................... | A61C 19/06 |
| | | | 433/29 |
| 2017/0072219 A1 | 3/2017 | Deisseroth et al. | |
| 2017/0312117 A1 * | 11/2017 | Shah ........................ | A61B 5/01 |
| 2019/0091061 A1 | 3/2019 | Radmand | |
| 2020/0170574 A1 * | 6/2020 | Radmand ............... | A61B 5/291 |

FOREIGN PATENT DOCUMENTS

| | | | |
|---|---|---|---|
| WO | 2009072123 A2 | 6/2009 | |
| WO | 2010006049 A1 | 1/2010 | |
| WO | 2013057594 A2 | 4/2013 | |
| WO | 2016094390 A1 | 6/2016 | |

OTHER PUBLICATIONS

Tobias Bruegmann, Tobias van Bremen, Christoph C. Vogt, Thorsten Send, Bernd K. Fleischmann, Philipp Sasse. Optogenetic control of contractile function in skeletal muscle. Nature Communications, 2015; 6: 7153 DOI: 10.1038/ncomms8153 (Year: 2015).*

Montgomery, K., Yeh, A., Ho, J. et al. Wirelessly powered, fully internal optogenetics for brain, spinal and peripheral circuits in mice. Nat Methods 12, 969-974 (2015) (Year: 2015).*

Trojanowski NF, Fang-Yen C. Simultaneous Optogenetic Stimulation of Individual Pharyngeal Neurons and Monitoring of Feeding Behavior in Intact C. elegans. Methods Mol Biol. 2015;1327:105-19. doi: 10.1007/978-1-4939-2842-2_9. PMID: 26423971; PMCID: PMC4862196 (Year: 2015).*

Fleury Curado, T. et al., Chemogenetic stimulation of the hypoglossal neurons improves upper airway patency, Sci Rep. 2017;7:44392. Mar. 10, 2017, doi:10.1038/srep44392, pp. 1-6.

Australian Patent Office, International Search Report for corresponding PCT Application No. PCT/AU2019/050532 mailed Aug. 12, 2019, pp. 1-5.

Australian Patent Office, International Preliminary Report on Patentability for corresponding PCT Application No. PCT/AU2019/050532 mailed Apr. 28, 2020, pp. 1-14.

Gundelach, L.A., et al. "Towards the Clinical Translation of Optogenetic Skeletal Muscle Stimulation" (2020) European Journal of Physiology 472:527-545.

Guilleminault, C. et al. "The Effect of Electrical Stimulation on Obstructive Sleep Apnea Syndrome" (1995) Chest 107 (1): 67-73.

Yeung, J. et al. "Task-Dependent Nerual Control of Regions Within Human Genioglossus" (2022) J. App. Physiol. 132: 527-540.

Randoph, M. et al. "Ageing and Muscular Dystrophy Differentially Affect Murine Pharyngeal Muscles in a Region-Dependent Manner" (2014) J. Physiol. 592(23): 5301-5315.

Lek, A. "Death After High-Dose rAAV9 Gene Therapy in a Patient with Duchenne's Muscular Dystrophy" (2023) New England J. Med. 389(13).

Ji, J. et al. "Comparative in vivo characterization of newly discovered myotropic adeno-associated vectors" (2024), Skeletal Muscle, 14(9).

Tabebordbar, M. et al. "Directed evolution of a family of AAV capsid variants enabling potent muscle-directed gene delivery across species" (2021) Cell 184(19): 4919-4938 (Tabebordbar).

Del Sol-Fernandez, S. et al. "Magnetogenetics: Remote Activation of Cellular Functions Triggered by Magnetic Switches" (2022) Nanoscale 14: 2091-2118 (Del Sol-Fernandez.

Huang, H et al. "Remote control of Ion Channels and Neurons through Magnetic-Field Heating of Nanoparticles" (2010) Nat Nanotech 5(8): 602-606.

Stanley, D et al. "Translocation and Dissemination of Commensal Bacteria in Post-Stroke Infection" (2016) Nat Med. 22(11).

* cited by examiner

SYSTEMS, DEVICES AND METHODS FOR THE TREATMENT OF ORAL AND PHARYNGEAL DISORDERS

CROSS-REFERENCE TO RELATED PATENT APPLICATIONS

The present application is a U.S. national stage application under 35 U.S.C. § 371 of PCT Application No. PCT/AU2019/050532, filed May 29, 2019, which claims priority to Australian Patent Application No. 2018901953, filed May 31, 2018. The disclosures of the aforementioned priority applications are incorporated herein by reference in their entireties.

FIELD OF THE INVENTION

The present invention relates to systems, devices and processes for intervention in oral and pharyngeal disorders. However, it will be appreciated that the invention is not limited to this particular field of use.

BACKGROUND OF THE INVENTION

Any discussion of the prior art throughout the specification should in no way be considered as an admission that such prior art is widely known or forms part of common general knowledge in the field.

Activation of excitable cells, such as neurons and muscle cells, can be achieved via the introduction of receptors or ion channels in these cells that respond to stimuli that are not usually present in the normal animal (including humans). These receptors and ion channels can be designed or selected to respond to non-physiological stimuli, such as light (optogenetics), chemical substances (chemogenetics), or a magnetic field (magnetogenetics), for example.

Optogenetics is the use of light to stimulate excitable cells, by genetically modifying these cells to express light-sensitive ion channels, or opsins, in their membranes.

Chemogenetics is the use of artificially engineered receptors that respond to non-physiological chemical stimuli to activate the excitable cells.

Magnetogenetics is the use of magnetic stimuli to stimulate the excitable cells, by genetically modifying these cells to express magnetically sensitive ion channels in their membranes.

The pharyngeal muscles surround the upper airway and are responsible to a range of critical functions including speech, swallowing, and maintaining patency of the upper airway, enabling respiration.

Obstructive sleep apnoea is a common sleep disorder in which muscle activity of the pharyngeal muscles is insufficient to maintain patency of the upper airway during sleep. The upper airway collapses repeatedly during sleep resulting in oxygen desaturation, that requires arousal to normalize. The results in sleep fragmentation, daytime sleepiness, increased risk of accidents and cardiovascular disease. Stimulation of the pharyngeal dilator muscles can widen the airway and maintain patency, including during sleep.

There are current treatments that rely on electrical stimulation of the dilator muscles in the tongue, whereby electrical stimulation activates the hypoglossal nerve, thereby causing the dilator muscles to contract and widen the upper airway. These systems are fully implanted and cannot provide non-invasive or minimally invasive muscle stimulation. Additionally, they are not effective for all people.

Other treatment methods, such as the delivery of continuous positive airway pressure or mandibular advancement splints, have reports of sub-optimal patient tolerance and adherence, or non-universal effectiveness.

Dysphagia is difficulty in swallowing. It may occur with or without pain. It can occur for many reasons but is commonly associated with neurological dysfunction of the pharyngeal or oesophageal muscles. This can occur in a range of neurological disorders, including multiple sclerosis, muscular dystrophy, Parkinson's disease, stroke, and spinal cord or brain injury. It can also occur after trauma or surgery, or in cancer, or as a result of cancer treatments. Current treatments involve physical therapy exercises, or surgical or pharmaceutical treatments that relax the oesophageal muscles to reduce distal blockage of the oesophagus.

Speech disorders involve difficulties in speaking or producing sounds fluently. A subset of patients with speech disorders acquire these as a result of dysfunction of the pharyngeal muscles, associated with neurological disorders such as stroke, or neuromuscular degenerative disorders.

It is an object of the present invention to overcome or ameliorate at least one of the disadvantages of the prior art, or to provide a useful alternative.

SUMMARY OF THE INVENTION

Herein are provided systems, devices, and methods for the treatment of oral and pharyngeal disorders. In some preferred embodiments, light-responsive opsin proteins able to activate either motor neurons innervating the pharyngeal muscle(s) or the muscle cells themselves are used, thereby inducing contraction of the pharyngeal muscles in response to a light stimulus. In other preferred embodiments, magnetic or chemical stimulus are used to induce contraction of the pharyngeal muscles.

According to a first aspect, the present invention provides a system for stimulating pharyngeal muscles, the system including means for activation of at least one ion channel formed in at least one of a muscle cell and a neural cell.

According to a second aspect, the present invention provides a method for stimulating the pharyngeal muscles, the method including: activation of at least one ion channel formed in at least one of a muscle cell and a neural cell.

Preferably, the ion channel opens when it is activated thereby causing muscle contraction. Preferably, the activation means activate an exogenous receptor linked to the ion channel.

According to a third aspect, the invention provides a system for inducing contraction of pharyngeal muscle cells, the system including: a delivery means configured to direct a stimulus to a target; a stimuli source, configured to provide the stimulus to the delivery means; and a controller operatively coupled to the stimulus source.

According to a fourth aspect, the invention provides a method for inducing contraction of pharyngeal muscle cells, the method including the step of directing a stimulus to a target, thereby to induce contraction of the muscles cells.

Preferably, the target is an ion channel. The ion channel is preferably formed in at least one of a pharyngeal muscle cell and a neural cell.

Preferably, the target is an exogenous receptor linked to the ion channel. This would preferably apply to a chemogenetic application or combination application including both chemical stimuli and another stimulus, such as light stimuli.

Preferably, the stimulus is light that acts on a cognate optogenetic target. Preferably the stimulus is a chemical substance that acts on a cognate chemogenetic target. Preferably, the stimulus is a magnetic field that acts on a cognate magnetogenetic target. In some embodiments, more than one of the mentioned stimuli may be used in combination. For example, light stimuli may be utilised during the night for treatment and chemical stimuli used during the day to turn off the receptors so that activation doesn't occur due to daylight.

Preferably the systems and methods are suitable for use as a therapy for disorders of the pharyngeal or oral musculature. Preferably the systems and methods are suitable for use as a therapy for obstructive sleep apnoea. Preferably, the systems and methods are suitable for use as a therapy for dysphagia.

Preferably, specific muscles or subregions of muscles are stimulated to provide targeted airway muscle control.

Preferably, the ion channels are photosensitive ion channels. Alternatively, the ion channels are sensitive to magnetic fields. Alternatively, the ion channels are sensitive to one or more chemical substances. In preferred embodiments, the ion channels are sensitive to one or more of the above.

Preferably, the ion channels are formed by delivery of genetic material into the muscle cell and/or neural cell. Preferably, the genetic material is delivered by local injection using a viral vector. The injection may be targeted to a specific location. Alternatively, the injection may be into a general region. In another embodiment, the genetic material is delivered by systemic delivery using a viral vector. Alternatively, the ion channels are formed by local delivery of genetic material by electroporation or other means. Preferably, the genetic material includes modified stem cells or encapsulated cells.

Preferably, the method according to the second or fourth aspect includes the step of forming ion channels in at least one of a pharyngeal muscle cell and a neural cell.

Preferably, the system according to the first or third aspect includes a mechanism for forming ion channels in at least one of a pharyngeal muscle cell and a neural cell.

Preferably, ion channels are targeted to the peripheral nerves that innervate the pharyngeal muscles. Alternatively, the ion channels are targeted to the pharyngeal muscle cells.

Preferably, additional chemical or genetic control mechanisms are provided to govern the activity of the photosensitive ion channels.

In some embodiments, the system is preferably activated in synchronisation with the respiratory cycle. In these, and other embodiment, the system may be activated on demand, either for defined periods or intermittently. In still further embodiments, the system is preferably activated in response to partial or complete upper airway obstruction as detected by an integrated pharyngeal pressure sensor or other means.

Preferably, the system includes a light source. The light source is preferably capable of generating red, amber, blue, or green light. Preferably, the ion channels are activated by red, amber, blue, or green light.

Preferably, the system delivers a light stimulus to activate the exogenous receptors linked to ion channels formed in pharyngeal muscle or neural cells. In some embodiments, the light stimulus is delivered via one or more intra-oral sources. In alternative embodiments the light stimulus is delivered via one or more transcutaneous sources. In still further embodiments, the light stimulus is delivered via one or more implanted sources, via an optical fibre or other means.

Preferably, the system includes an oral appliance. The appliance is preferably removable. Preferably, the removable appliance is worn primarily or solely during sleep. Preferably, the appliance includes a rechargeable power source.

Preferably, the oral appliance includes a channel for releasable engagement with the teeth of the user. Alternatively, the oral application includes a loop for tooth engagement.

In an alternative embodiment, the system includes a subcutaneously implanted device. Preferably, the implanted device activates or stimulates the ion channels invasively or minimally invasively.

Preferably, the system includes both internal and external components. The internal components may include removable and/or implanted components. External components may include a power source. Electrical power may be supplied from the power source to the internal components using inductive power or RF power delivery.

Preferably, the system includes at least one sensor. The sensor is preferably configured to produce an electrical signal representative of the state of the target or its environment. Preferably, the sensor is configured to deliver the signal to the controller, wherein the controller is further configured to interpret the signal from the sensor and adjust the stimuli directed at the target. Preferably, the system is configured to transmit sensed information to an external device for analysis or viewing by a clinician.

Preferably, the system includes at least one sensor for monitoring a condition of a user. Such conditions may include, for example, the respiratory cycle of the user, breathing, cessation of breathing, apnoea, hypopnea, diaphragm movement, muscle cell activity, neural cell activity, impedance across chest, airway pressure, temperature, pharyngeal narrowing, or pharyngeal collapse. For example, airway pressure can indicate that an airway is partially or completely occluded. In a further example, an accelerometer could be used to detect vibrations of the airway that may indicate the patient is snoring and/or provide information about the severity of the patient's snoring.

Preferably, when a predetermined condition is sensed, delivery of stimuli to the target is activated to induce contraction or relaxation of the pharyngeal muscles. Advantageously, specific muscle or neural cells can be targeted, allowing control of specific regions of pharyngeal muscles to effect airway stiffening or dilation.

Alternatively, the controller may utilise a timer to deliver a predetermined stimulation strategy. In other embodiments, the delivery of stimuli may be controlled manually. This may be suitable, for example, when the stimulus is chemical in nature or for conditions such as swallowing difficulties.

Preferably, stimulation of muscles is targeted to a specific location. For example, the location where a collapse is happening in the airways. This may be achieved by providing stimuli to ion channels in the target area only. Alternatively, this may be achieved by providing stimuli to the entire pharyngeal area but where ion channels have only been formed in the area targeted for stimulation. Should the user requirements change over time, additional ion channels can be formed in new areas for stimulation.

Preferably, the system includes a transmission means for transmitting sensed information and/or user parameters for access by a clinician or technician. The system may also or instead include a data storage means for storing sensed data and/or user parameters for subsequent access and/or review. Subsequent access to the stored data may be via download or wireless transmission. Advantageously, ongoing data collected can be used to monitor the patient's condition and effectiveness of treatment.

Preferably, the system may include at least one monitoring module. These may be used to monitor and/or store various user parameters and/or sensed information as required. The module may be configured to releasably connect to the oral appliance. Alternatively, the module may be used simultaneously with the oral appliance. The monitoring module preferably includes a power source.

BRIEF DESCRIPTION OF THE DRAWINGS

Embodiments of the invention will now be described, by way of example only, with reference to the accompanying drawings as follows.

PREFERRED EMBODIMENT OF THE INVENTION

Although the invention has been described with reference to certain embodiments detailed herein, other embodiments can achieve the same or similar results. Variations and modifications of the invention will be obvious to those skilled in the art and the invention is intended to cover all such modifications and equivalents.

Preferred embodiments of the invention will now be described, by way of example only, with reference to the accompanying drawings.

Figure 1:
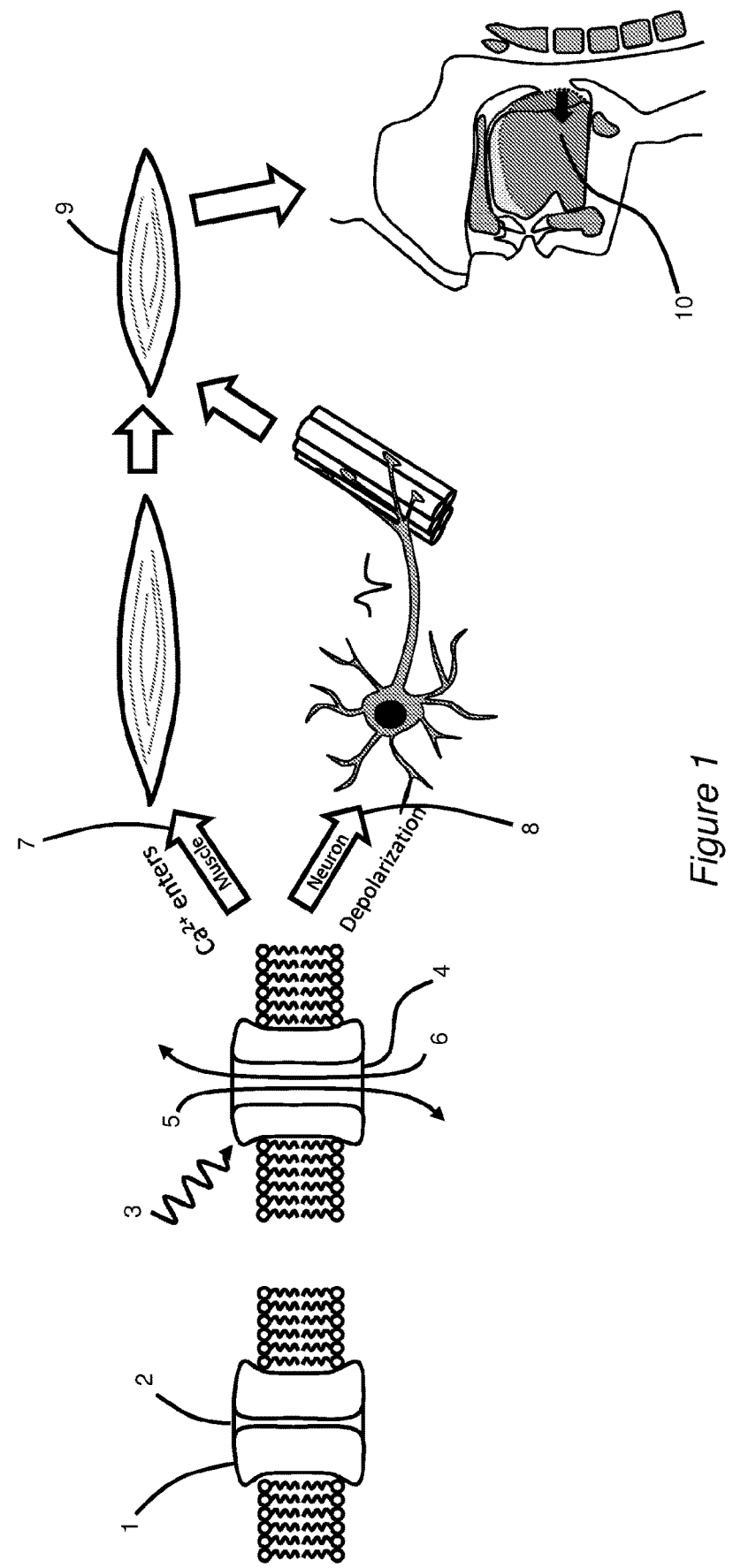
FIG. 1 is a diagram showing stimulation of pharyngeal muscles using excitation of ion channels formed in muscle cell or neural cell membrane for the treatment of sleep apnoea.

As best shown in FIG. 1, ion channels 1 formed in a muscle cell or neural cell are closed 2 when the cell is inactive. A stimulus 3, in the form of light, magnetic field, or chemical, is applied and causes the ion channel to open 4. This allows ions to flow into 5 and out of 6 the cell, thereby activating the cell. When the ion channel is formed in a muscle cell 7, activation of the muscle cell causes $Ca^{2+}$ to enter the muscle. This triggers relative motion of actin and myosin, causing muscle cell contraction. Alternatively, when the ion channel is located in a neural cell 8, activation of the neural cell sends an action potential to the neuromuscular junction on the corresponding muscle cell, activating the muscle cell. This similarly causes $Ca^{2+}$ to enter the muscle, triggering relative motion of actin and myosin, and causing muscle cell contraction. In this example application, for the treatment of sleep apnoea, the resulting contraction of the pharyngeal dilator muscles 9 causes opening of the airway 10. In alternative applications, such as for the treatment of dysphagia or speech disorders, stimulation may be directed towards different muscles and result in different actions, such as tongue movement or swallowing.

The ion channels do not exist naturally and are required to be formed in the user's muscle cells and/or neural cells. This may occur prior to application of the invention. Alter-natively, the systems and methods according to the invention may respectively include a mechanism or step for forming ion channels in at least one of a muscle cell and a neural cell.

The ion channels are formed by delivery of genetic material into the muscle cell and/or neural cell. In some embodiments, the genetic material is delivered by local injection using a viral vector. The injection may be targeted to a specific location. Alternatively, the injection may be into a general region. In another embodiment, the genetic material is delivered by systemic delivery using a viral vector. Alternatively, the ion channels are formed by local delivery of genetic material by electroporation or other means. Preferably, the genetic material includes modified stem cells or encapsulated cells.

Figure 2:
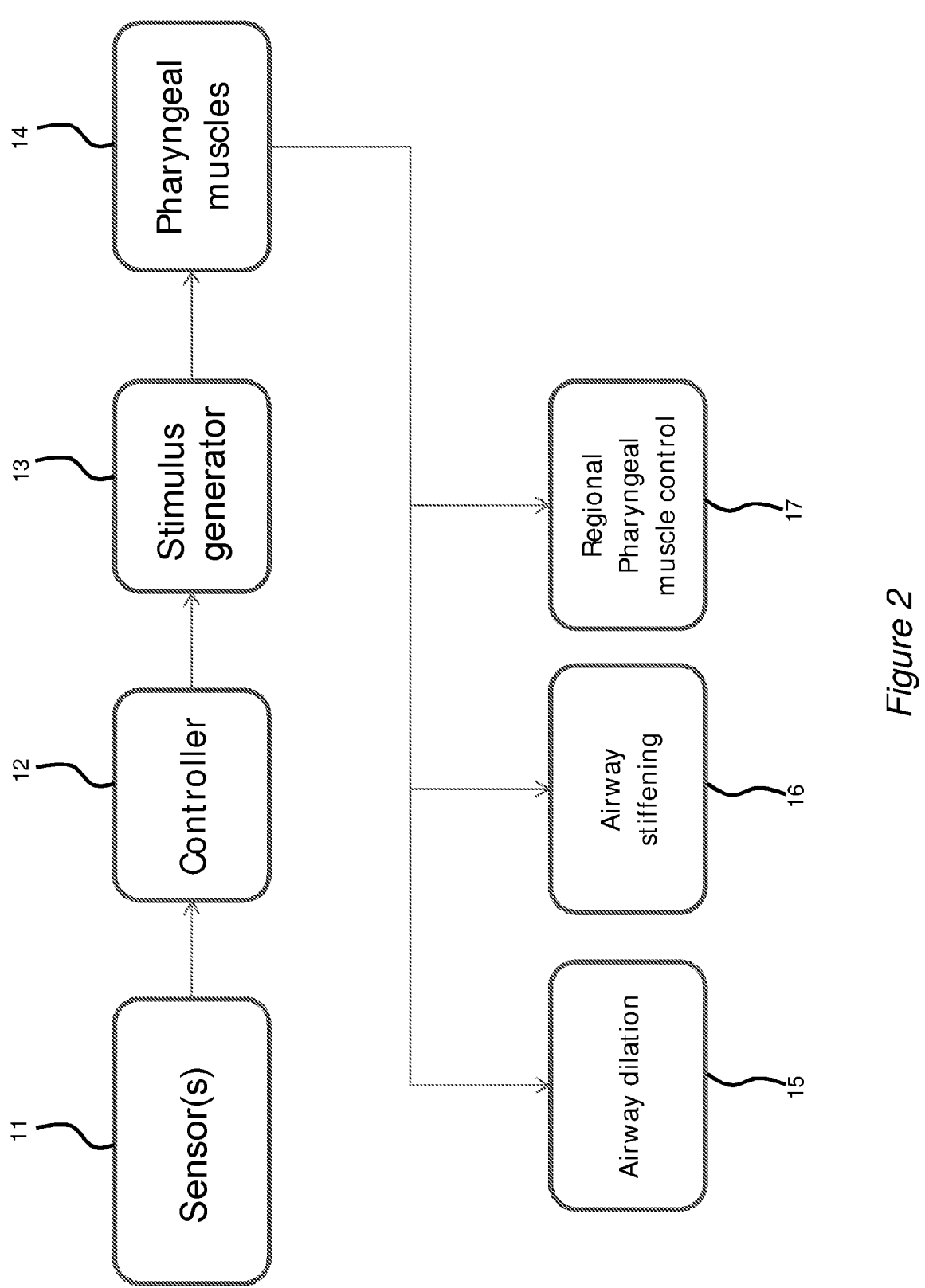
FIG. 2 is a flow chart showing a method of stimulating pharyngeal muscles according to the invention.

Referring now to FIG. 2, a preferred method of stimulating pharyngeal muscles according to the invention is shown. In this embodiment, sensors 11 detect a predetermined scenario such as pharyngeal narrowing, pharyngeal collapse, or a phase of a respiratory cycle. An associated controller 12 sends a signal to a stimulus generator 13, which may be connected directly or via a wireless connection. This signal directs the stimulus generator to provide stimulus in the form of light, chemicals, or a magnetic field to the ion channels which have been formed in the user's cells. As above, the provision of stimulus to the ion channels, activates the associated cells, thereby causing contracting of the pharyngeal muscles 14. As shown in the diagram, this muscle contraction can be used to achieve airway dilation 15, airway stiffening 16, or regional pharyngeal muscle control 17 in the user.

Figure 3:
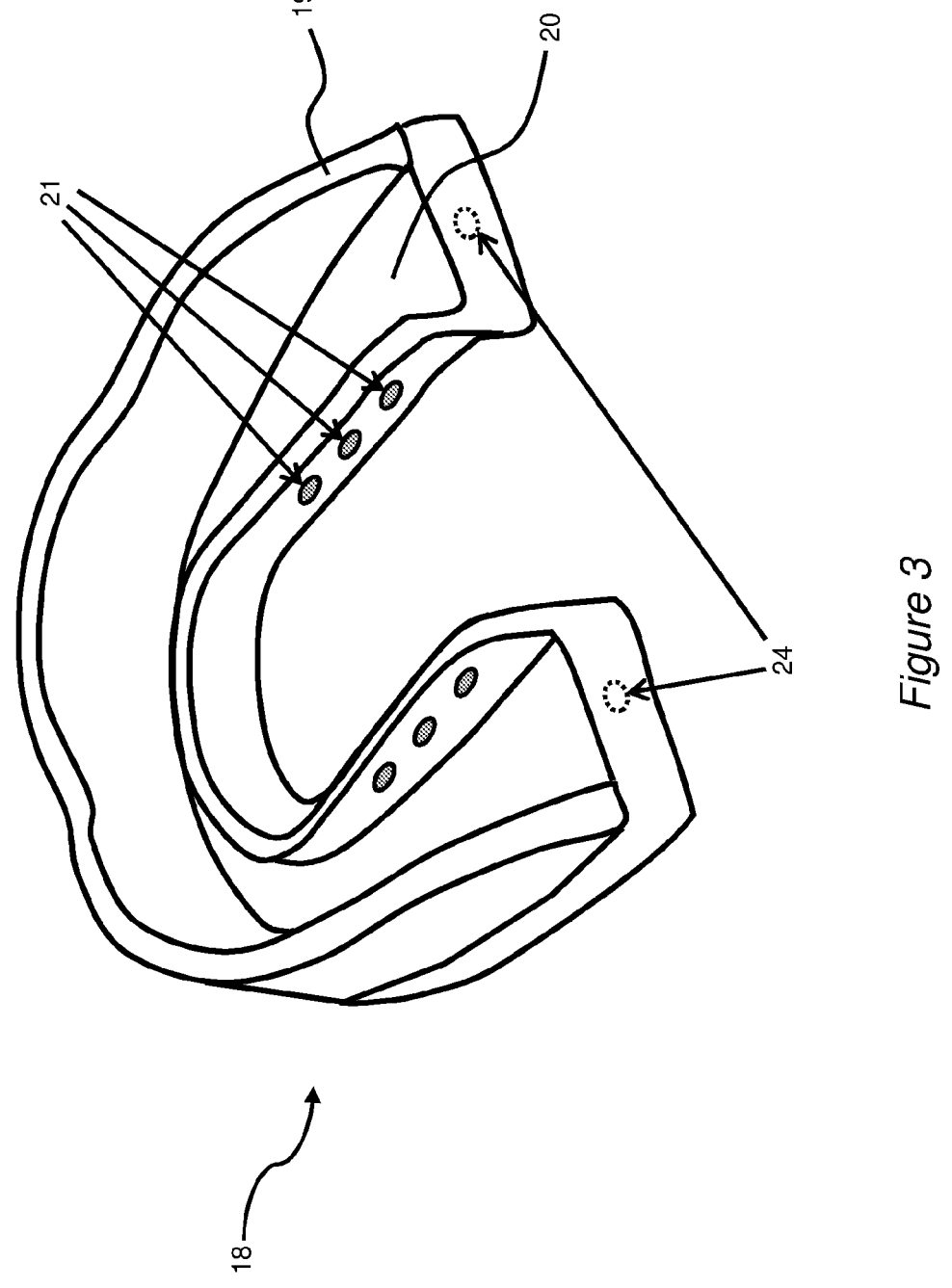
FIG. 3 is a rear perspective view of a first embodiment of an oral appliance according to the invention.
Figure 4:
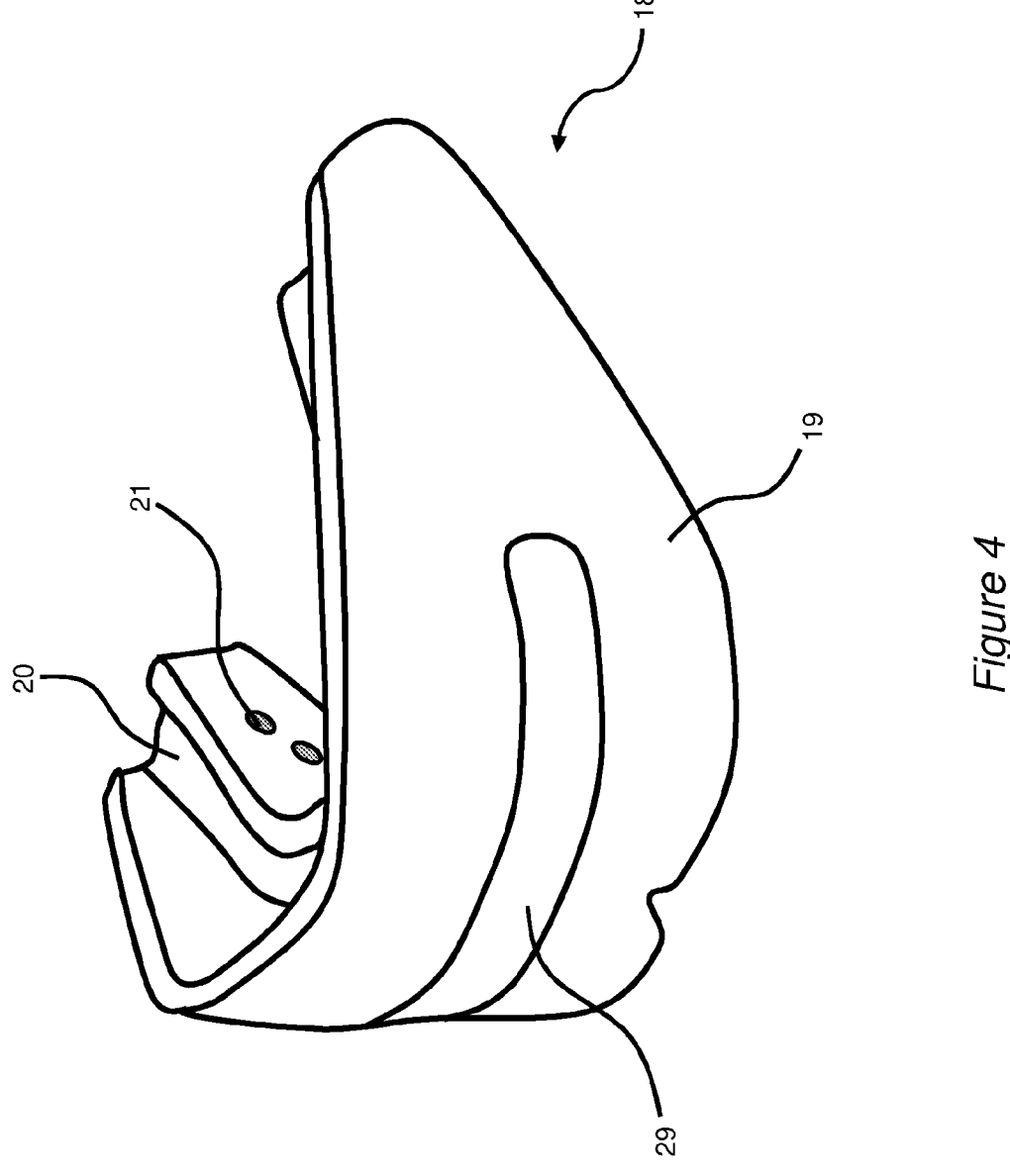
FIG. 4 is a front perspective view of the oral appliance shown in FIG. 3.

As best shown in FIGS. 3 and 4, one preferred embodiment of the system 18 includes an oral appliance or device 19. The device includes a channel 20 configured to comfortably engage over a user's teeth, thereby assisting retention of the device in the mouth. The device 19 includes a delivery means, shown in the form of a plurality of delivery sites 21, for delivering stimulus from a stimulus source (not shown) to at least one ion channel formed in a muscle cell or neural cell.

Figure 5:
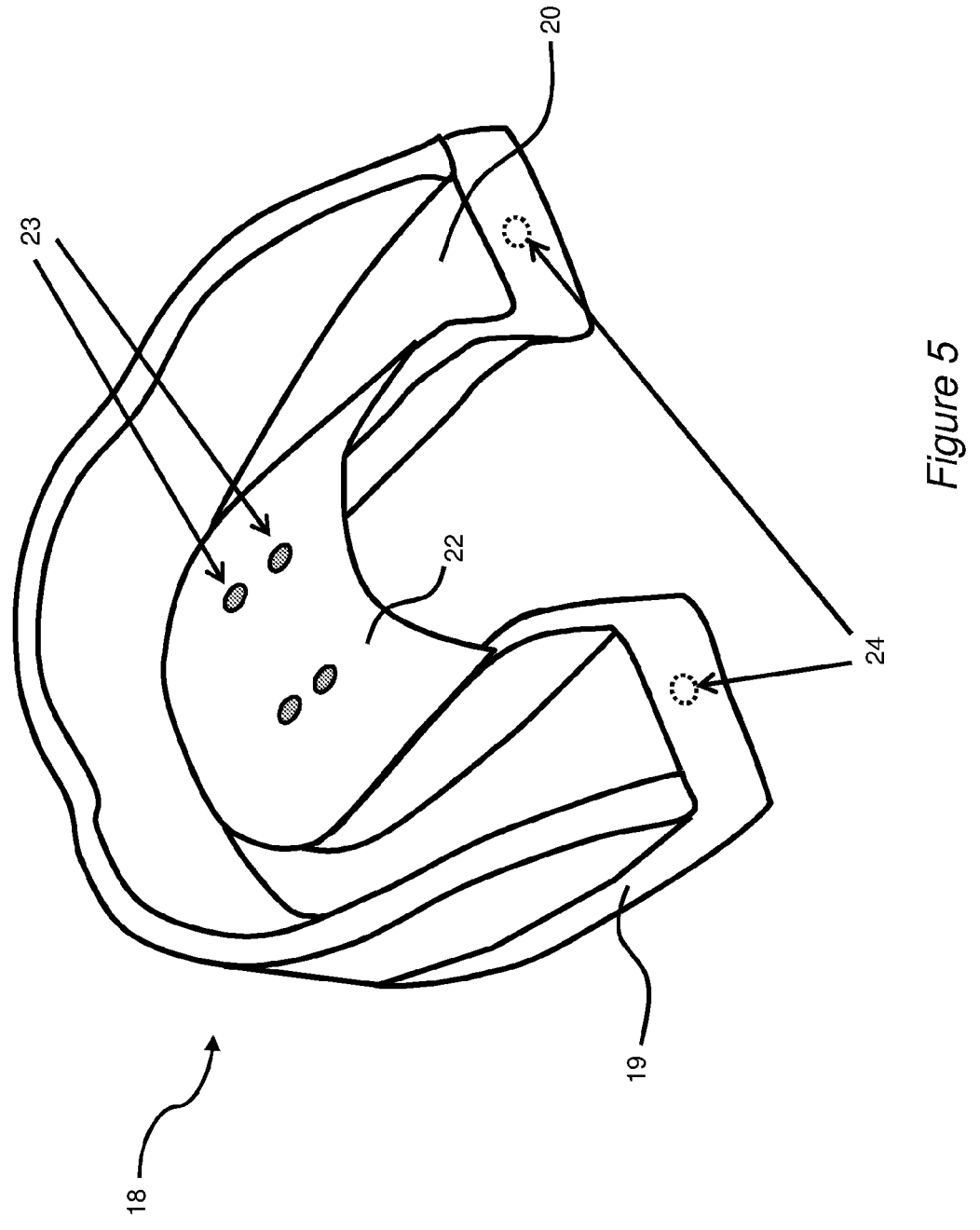
FIG. 5 is a rear perspective view of a second embodiment of an oral appliance according to the invention.

Alternatively, another embodiment of the device shown in FIG. 5, includes a roof portion 22 that can provide additional or alternative delivery site locations 23 to the embodiment shown in FIGS. 3 and 4. In a still further embodiment (not shown), the device may be in a form similar to an orthodontic retainer or plate, with wire loops or another releasable fastening mechanism to hold the device in the user's mouth.

It will be appreciated that the stimulus may be light, chemical or magnetic in nature, with the delivery means and stimulus source corresponding to the stimulus being delivered. For example, where the stimulus is light, the system may generate red, amber, blue, or green light and the ion channels are responsive to red, amber, blue, or green light.

For chemical stimulus, one technique that could be used is to target an engineered receptor that is activated solely by synthetic ligands (RASSL). The most common version of this is designer receptors exclusively activated by designer drugs (DREADDS), which targets g-protein coupled receptors. Commonly clozapine-N-oxide (CNO) is the ligand, and clozapine sensitive receptors are engineered, and then expressed in the target cell. The receptors are activated by delivering the ligand, clozapine-N-oxide, to the animal, often intraperitoneally, although there are many options (even eye drops). When used with the invention, this could be delivered from a local reservoir (timed to release at certain times of the day in specific locations in the tongue, for example), via slow biodegradable materials as part of an oral device, nanoparticles delivery orally etc. The engineered receptors can be delivered the same way as optogenetic constructs, that is, using viral vectors, via local injection, or other routes. In relation to the invention, the genetic material to create the engineered receptors would likely be delivered using local injection, but electroporation or other techniques could also be used. The genetic material for the receptors could also be targeted to either neural on muscle cell, by use of a cell-type specific promotor. Other RASSLs exist that are activated by a range of drugs, but CNO is the most common drug used.

In some embodiments, more than one of the mentioned stimuli may be used in combination. For example, light stimuli may be utilised during the night for treatment and chemical stimuli used during the day to turn off the receptors so that ion channels are not activated due to daylight.

The device includes a controller (not shown) operatively coupled to the stimulus source. In some embodiments, the controller may utilise a timer to deliver a predetermined stimulation strategy. In other embodiments, the delivery of stimulus may be controlled manually. This may be suitable, for example, when the stimulus is chemical in nature or for treatment of conditions such as swallowing difficulties.

The device 19 includes integrated sensors 24 for identifying a treatment situation. Sensors may be used to monitor any one or more of the following parameters: the respiratory cycle of the user, breathing, cessation of breathing, apnoea, hypopnea, diaphragm movement, muscle cell activity, neural cell activity, impedance across chest, airway pressure, temperature, pharyngeal narrowing, or pharyngeal collapse. For example, airway pressure can indicate that an airway is partially or completely occluded. An accelerometer may be used to detect vibrations of the airway. These vibrations may indicate that the patient is snoring and/or provide information about the severity of the patient's snoring.

Each sensor is configured to produce an electrical signal representative of the parameter being monitored. The sensor is configured to deliver the signal to the controller, wherein the controller is further configured to interpret the signal from the sensor and adjust the stimulus directed at the target. That is, when a predetermined condition is sensed, delivery of stimulus to the target ion channels is activated to induce contraction or relaxation of the pharyngeal muscles. Advantageously, specific muscle or neural cells can be targeted, allowing control of specific regions of pharyngeal muscles to effect airway stiffening or dilation, as required.

In the embodiments shown in FIGS. 3 and 5, sensors 24 are shown at the ends of the device and these would be located near the back of a user's mouth when in use. However, it will be appreciated that the sensors may be located anywhere on the device. The location of the sensors may depend upon the parameters which require monitoring.

Figure 6:
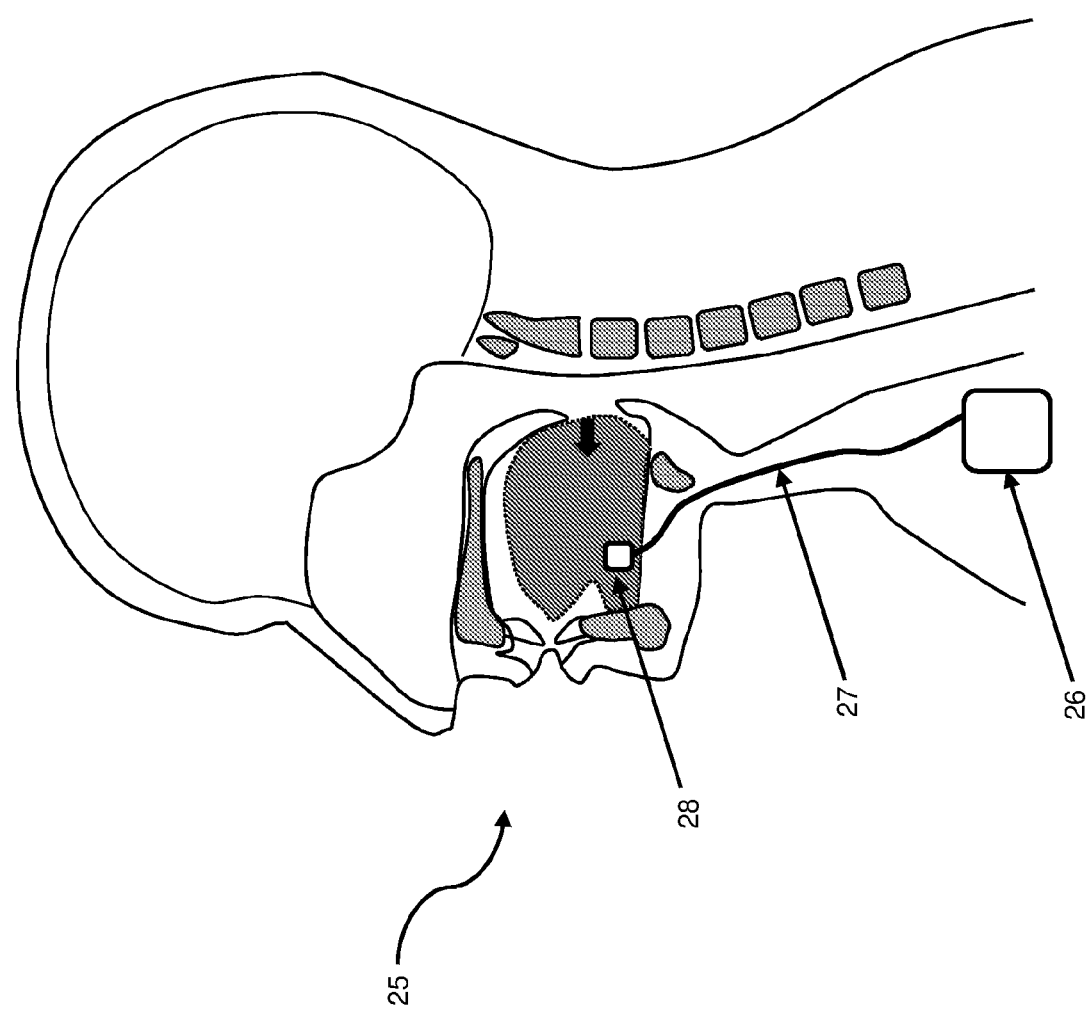
FIG. 6 is a side view of an oral appliance according to a third embodiment of the invention shown implanted in a user.

As shown in FIG. 6, another preferred embodiment of the system includes an implantable system 25. The system 25 includes an implanted control component 26, which may include a power source, stimulus source, and control module. The control component 26 may be connected 27 wirelessly or via a wired or fluid connection (for example, for chemical stimuli) to stimulus delivery sites 28 located in the oral cavity. The stimulus delivery sites may be implanted, for example in the tongue, and provide stimulus invasively. Alternatively, the stimulus delivery may occur via a minimally invasive approach, for example with the delivery sites located on a removable component which is placed in the oral cavity. Stimulus delivered from the delivery sites activates or stimulates the ion channels.

The system may also be configured to transmit sensed information to an external device for analysis or viewing by a clinician.

A user may require monitoring for a temporary period of time. In some embodiments, the system may include monitoring modules that include a sensor and power source 29. Such modules can be connected to the system 18, 25 or used separately to gather information about the user. In some embodiments, the system includes a transmission means for transmitting sensed information and/or user parameters for access by a clinician or technician. The system may also or instead include a data storage means for storing sensed data and/or user parameters for subsequent access and/or review. Subsequent access to the stored data may be via download or wireless transmission. Advantageously, ongoing data collected can be used to monitor the patient's condition and effectiveness of treatment.

The system may include a detachable monitoring module that can be connected and detached from the oral appliance as required. These may be used to monitor and/or store various user parameters and/or sensed information as required.

Figure 7:
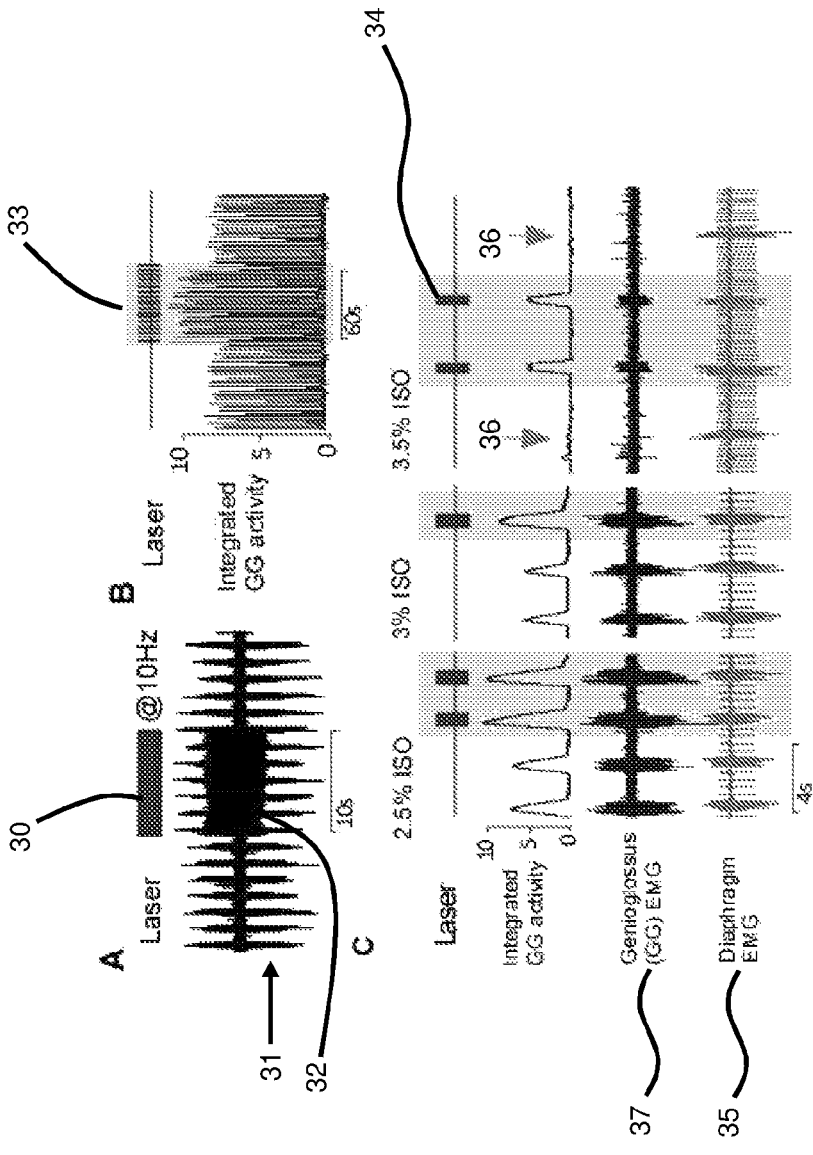
FIG. 7 is a diagram showing the measured effect of pharyngeal muscle stimulation by optical activation.

FIG. 7 is a series of diagrams showing the effect of pharyngeal muscle stimulation by optical activation.

In the experiment leading to the data shown in FIG. 7, the following methods were used. Rat genioglossus muscle was transduced with Channel Rhodopsin 2 (ChR2) fused to a fluorescent reporter (yellow fluorescent protein, YFP) after local injection of 10 μL solution containing an adeno-associated virus (AAV) serotype 9 with a robust pan-cellular "CAG" promotor (chicken beta-actin gene). The expression vector (AAV9-CAG-ChR2-YFP) was suspended in a solution of phosphate buffered saline. Functional ChR2 expression was observed four weeks after the intramuscular injection. Electromyographic activity of the genioglossus muscle was evoked by light stimulation applied to the tongue surface with a 470 nm laser operating at 10 Hz, over a range of pulse widths (1 to 20 ms). Effective stimulation occurred with a laser power of 1 to 10 mW.

FIG. 7A shows an electromyographic (EMG) measurement of genioglossus activity during the respiratory cycle. A light stimulus at 10 Hz is applied at the tongue surface for 10 seconds, represented by the blue bar 30. Prior to the stimulation being applied, the genioglossus activity is phasic 31, corresponding to the cyclic nature of the respiratory cycle. During the stimulation, tonic genioglossus activity 32 is also evoked. When the light stimulation is ceased, the tonic activity also ceases.

FIG. 7B shows integrated genioglossus activity during the respiratory cycle. A light stimulus is applied during inspiration only for 60 seconds, as shown by the plurality of blue lines 33. As shown, this stimulus evokes increased activity of the genioglossus synchronised with inspiration.

FIG. 7C shows light stimulus 34 applied in synchronisation with the respiratory cycle using diaphragm EMG signal 35 to represent the respiratory cycle. Three different levels of isoflurane (ISO) are used, namely 2.5% ISO, 3% ISO and 3.5% ISO, to cause corresponding levels of muscle deactivation.

Comparing the integrated genioglossus activity when 2.5% ISO is applied to the integrated genioglossus activity in FIG. 7B, it is seen that the activity is similar. When 3% ISO is applied, the integrated genioglossus activity is decreased. When 3.5% ISO is applied, the integrated genioglossus activity is further decreased, resulting in atonia 36 of the genioglossus muscles. The decreased muscle activity results in a situation where the airway may partially or completely close.

As the light stimulus 34 is applied, genioglossus activation is evoked. As shown in the genioglossus EMG trace 37 and the diaphragm EMG trace 35, this genioglossus activity supplements inspiratory activity in the 2.5% and 3% ISO applications and provides inspiratory activity in the absence of background inspiratory activity in the 3.5% ISO application.

In use, for the treatment of sleep apnoea for example, the device 19 is inserted by the user into their mouth before going to sleep. Here, the device is worn primarily or solely during sleep, however for other conditions it is appreciated that the device 19 may be worn at other times. For example, in treatment of swallowing disorders, the appliance may be worn during meal times. Alternatively, the system may be implanted, as shown in FIG. 6.

When a predetermined condition is sensed, for example, a predetermined level of airway pressure indicating partial occlusion of the airways, stimuli is delivered to identified ion channels. This causes the ion channels to open, thereby causing muscle contraction in the target muscles. Alternatively, the system may be activated in synchronisation with the respiratory cycle.

Specific muscles or subregions of muscles are stimulated to provide targeted muscle control. For example, muscle stimulation may be targeted to a location where a collapse is occurring in the airways. This may be achieved by providing stimuli to ion channels in the target area only. Alternatively, this may be achieved by providing stimuli to the entire pharyngeal area but where ion channels have only been formed in the area targeted for stimulation. Should the user requirements change over time, additional ion channels can be formed in new areas requiring stimulation.

Further applications of the invention may include targeting genetically-defined pharyngeal afferents to suppress coughs or hiccups, effect swallowing, or boost genioglossus EMG in sleep. For example, involuntary coughing at night may be suppressed by chronic chemogenetic inhibition of pharyngeal afferents. Genioglossus EMG activity may be boosted by either acute or chronic activation of negative pressure pharyngeal afferents.

Definitions

In describing and claiming the present invention, the following terminology has been used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

As used herein the term "about" can mean within 1 or more standard deviation per the practice in the art. Alternatively, "about" can mean a range of up to 20%. When particular values are provided in the specification and claims the meaning of "about" should be assumed to be within an acceptable error range for that particular value.

In the context of the invention the term "subject" includes any human or non-human animal. The term "non-human animal" includes all vertebrates, for example mammals and non-mammals, such as non-human primates, horses, cows, dogs, etc.

In the context of the present invention, the words "comprise", "comprising" and the like are to be construed in their inclusive, as opposed to their exclusive, sense, that is in the sense of "including, but not limited to".

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Other than in the operating examples, or where otherwise indicated, all numbers expressing quantities of ingredients or reaction conditions used herein are to be understood as modified in all instances by the term 'about'.

Unless specifically stated otherwise, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled", "connected," "attached", and/or "joined", along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other. In contrast, when a component is referred to as being "directly coupled", "directly attached", and/or "directly joined" to another component, there are no intervening elements present.

Various aspects of the present devices, systems, and methods may be illustrated with reference to one or more exemplary embodiments. As used herein, the term "exemplary" means "serving as an example, instance, or illustration," and should not necessarily be construed as preferred or advantageous over other embodiments disclosed herein.

Thus, while there has been described what are believed to be the preferred embodiments of the disclosure, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The recitation of a numerical range using endpoints includes all numbers subsumed within that range (e.g., 1 to 5 includes 1, 1.5, 2, 2.75, 3, 3.80, 4, 5, etc.).

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The invention claimed is:

1. A system comprising:
a mechanism configured to form at least one ion channel in at least one of a pharyngeal muscle cell and a neural cell associated with a pharyngeal muscle cell, such that the at least one channel opens and closes in response to a stimulus source;
an oral appliance; and
a controller operably coupled to the oral appliance and programmed to operate the stimulus source;
wherein the oral appliance comprises the stimulus source configured for direct in vivo activation of the at least one ion channel formed in the at least one pharyngeal muscle cell or at least one motor neural cell associated with a pharyngeal muscle cell, thereby causing the at least one ion channel to open and induce contraction of at least one muscle cell; and
wherein the oral appliance comprises a channel configured to engage over a user's teeth.

2. The system according to claim 1, wherein the at least one channel is photosensitive or magnetically sensitive such that the at least one ion channel opens and closes in response to light or a magnetic field, and the stimulus source provides a stimulus selected from one or more of: light that acts on a cognate optogenetic target; and a magnetic field that acts on a cognate magnetogenetic target.

3. The system according to claim 2,
wherein the stimulus is light that acts on the cognate optogenetic target;
wherein the light is any one of red, amber, blue, or green light; and
wherein the ion channel is able to be activated or deactivated by any one or more of red, amber, blue, or green light.

4. The system according to claim 1, wherein the system is configured to selectively deliver a control stimulus to the at least one ion channel for selective in vivo activation or deactivation of the at least one ion channel.

5. The system according to claim 4, wherein the control stimulus is optical, chemical, genetic, or physical.

6. The system according to claim 1,
wherein the at least one ion channel is only formed in at least one location selected for muscle cell stimulation.

7. The system according to claim 1,
wherein the stimulus is delivered only to ion channels formed in at least one location selected for muscle cell stimulation and not to an ion channel formed in any other location.

8. The system according to claim 1, including at least one sensor for monitoring at least one predetermined treatment situation of a user, wherein the at least one predetermined treatment situation is selected from: the respiratory cycle of the user, breathing, cessation of breathing, apnea, hypopnea, diaphragm movement, muscle cell activity, neural cell activity, impedance across chest, chest movement, abdominal movement, airway pressure, temperature, pharyngeal narrowing, or pharyngeal collapse.

9. The system of claim 8, wherein the at least one sensor is an accelerometer for detecting vibrations of the airway.

10. The system according to claim 1, wherein at least part of the oral appliance is implantable.

11. The system of claim 1, wherein the oral appliance is an orthodontic retainer or orthodontic plate.

12. The system of claim 1, wherein the oral appliance further comprises a releasable fastening mechanism to hold the oral appliance in an oral cavity of the user.

13. The system of claim 1 further comprising a plurality of intraoral delivery sites positioned proximate to a pharyngeal muscle cell or a neuron associated with a pharyngeal muscle cell and configured to deliver the direct, in vivo stimulus to at least one ion channel; wherein the stimulus source is operably connected to the delivery sites to provide the stimulus directly at or through the delivery sites.

14. The system of claim 1, wherein the stimulus source is configured for direct, in vivo activation of at least one ion channel formed in at least one human pharyngeal muscle cell or at least one human motor neural cell associated with a human, pharyngeal muscle cell.

15. The system of claim 1, wherein the mechanism is configured to deliver genetic material to the at least one pharyngeal muscle cell or at least one motor neural cell associated with a pharyngeal muscle cell, thereby forming the at least one ion channel.

16. The system of claim 15, wherein the mechanism is configured to inject a viral vector into the at least one pharyngeal muscle cell or at least one motor neural cell associated with a pharyngeal muscle cell or electroporate the at least one pharyngeal muscle cell or at least one motor neural cell associated with a pharyngeal muscle cell.

17. The system of claim 1, wherein the mechanism is configured to deliver nanoparticles to the at least one pharyngeal muscle cell or at least one motor neural cell associated with a pharyngeal muscle cell, thereby forming the at least one ion channel.

18. A system for inducing contraction of at least one pharyngeal muscle cell, the system including:
   a mechanism configured to form at least one ion channel that is photosensitive or magnetically sensitive in at least one of a pharyngeal muscle cell and a neural cell associated with a pharyngeal muscle cell;
   an oral appliance configured to deliver an in vivo stimulus to the at least one ion channel formed in the at least one of a pharyngeal muscle cell and a neural cell associated with a pharyngeal muscle cell, thereby to induce contraction of at least one muscle cell;
   a stimulus source, configured to provide the stimulus through the oral appliance; and
   a controller operatively coupled to the stimulus source and programmed to operate the stimulus source;
   wherein the stimulus is selected from one light that acts on a cognate optogenetic target comprising the at least one ion channel and a magnetic field that acts on a cognate magnetogenetic target comprising the at least one ion channel.

19. A method for inducing contraction of at least one pharyngeal muscle cell in a human subject, the method including the steps of:

forming at least one ion channel that is photosensitive or magnetically sensitive in at least one of a pharyngeal muscle cell and a motor neural cell associated with a pharyngeal muscle cell in the human subject; and
delivering an in vivo stimulus directly to the at least one ion channel thereby causing the at least one ion channel to open and induce contraction of at least one muscle cell;
wherein the stimulus is selected from one or more of: light that acts on a cognate optogenetic target comprising the at least one ion channel; and a magnetic field that acts on a cognate magnetogenetic target comprising the at least one ion channel; and
detecting at least one predetermined treatment situation of the human subject, and
thereafter performing the step of delivering the stimulus, wherein the at least one predetermined treatment situation is selected from: the respiratory cycle of the user, breathing, cessation of breathing, apnea, hypopnea, diaphragm movement, muscle cell activity, neural cell activity, impedance across chest, chest movement, abdominal movement, airway pressure, temperature, pharyngeal narrowing, or pharyngeal collapse.

20. The method according to claim 19,
   wherein the stimulus is light that acts on a cognate optogenetic target;
   wherein the light is any one of red, amber, blue, or green light; and
   wherein the ion channel is able to be activated or deactivated by any one or more of red, amber, blue, or green light.

21. The method according to claim 19, including the step of:
   selectively delivering a control stimulus to the at least one ion channel, thereby to selectively allow or prevent contraction of the at least one muscle cell.

22. The method according to claim 21, wherein the control stimulus is optical, chemical, genetic, or physical.

23. The method according to claim 19,
   wherein the at least one ion channel is only formed in at least one location selected for pharyngeal muscle cell stimulation.

24. The method according to claim 19,
   wherein the step of delivering a stimulus includes delivering the stimulus only to ion channels formed in a location selected for pharyngeal muscle cell stimulation and not to an ion channel formed in any other location.

25. The method according to claim 19, wherein the ion channel is formed by delivery of genetic material into the pharyngeal muscle cell or the neural cell.

26. The method according to claim 19, wherein the method is suitable for use as a therapy for obstructive sleep apnea.

27. The method of claim 19, wherein the ion channel is formed by delivery of nanoparticles into the pharyngeal muscle cell or the neural cell.

28. A method of treating obstructive sleep apnea in a human subject comprising:
   (i) delivering to the human subject a direct, in vivo stimulus to at least one of pharyngeal muscle cell or a motor neural cell associated with a pharyngeal muscle cell in the oral cavity of the subject, thereby inducing contraction of the at least one pharyngeal muscle cell by forming an ion channel in the at least one pharyngeal muscle cell, wherein the ion channel is photosensitive or magnetically sensitive; and (ii) implanting a removable oral appliance in the human subject prior to step (i), wherein the removable oral appliance is configured to fit over the teeth of the human subject;

wherein the stimulus is selected from one or more of: light that acts on a cognate optogenetic target comprising the at least one ion channel and a magnetic field that acts on a cognate magnetogenetic target comprising the at least one ion channel.

* * * * *